United States Patent
Spellane

(10) Patent No.: US 6,365,034 B1
(45) Date of Patent: *Apr. 2, 2002

(54) HIGH THROUGHPUT ELECTROCHEMICAL TEST FOR MEASURING CORROSION RESISTANCE

(75) Inventor: Peter J. Spellane, Ardsley-on-Hudson, NY (US)

(73) Assignee: Polymer Alloys LLC, Ardsley-on-Hudson, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/428,177

(22) Filed: Oct. 27, 1999

Related U.S. Application Data

(63) Continuation of application No. 08/852,649, filed on May 7, 1997.
(60) Provisional application No. 60/106,525, filed on Oct. 31, 1998.

(51) Int. Cl.$^7$ .......................... G01N 27/26; G01N 27/48
(52) U.S. Cl. .................... 205/775.5; 204/404; 204/434; 205/791; 205/791.5
(58) Field of Search .................................. 204/404, 434; 205/775.5, 776, 776.5, 777, 790.5, 791, 791.5

(56) References Cited

U.S. PATENT DOCUMENTS

| | | |
|---|---|---|
| 3,242,064 A | 3/1966 | Byrne |
| 4,095,176 A | 6/1978 | Maes et al. |
| 4,294,667 A | 10/1981 | Yamamoto et al. .......... 204/1 T |
| 4,806,849 A * | 2/1989 | Kihira et al. |
| 4,863,571 A | 9/1989 | Chambaere |

FOREIGN PATENT DOCUMENTS

| | | |
|---|---|---|
| WO | WO 97/03127 | 1/1997 |

OTHER PUBLICATIONS

Wu et al, "A study on the electrochemical inhomogeneity of organic coatings", Progress in Organic Coatings, 1995, pp. 379–389, vol. 25, Elsevier Science S.A., Switzerland.*
"Here's a high–throughput method to screen catalyst compositions for selectivity and activity", Chemtech, Sep. 1999, p. 5.
"Combinatorial Test of Corrosion", Science, vol. 283, Jan. 8, 1999, p. 165.
"Combinatorial methodology holds promise for the discovery of improved catalysts for polymerization reactions", Chemtech, Jul. 1999, p. 46.
Corrosion Chemistry, G.R. Brubaker, ed., ACS Symposium Series 89, 1979, month unavailable, pp. 68–73.
Corrosion Engineering, Third Edition, M.G. Fontana, McGraw–Hill, 1986, month unavailable, pp. 469–473.

(List continued on next page.)

*Primary Examiner*—T. Tung

(57) ABSTRACT

A high throughput electrochemical test method for determining the resistance to corrosion of a metal article coated with a resinous coating which comprises:

(a) making, as the working electrode in an electrochemical cell which also comprises a reference electrode, a counter-electrode and an electrolytic solution, one or more metal articles comprising a plurality of coated areas thereon, with the proviso that a portion of the coating does not exist on the metal thereby allowing for the ultimate passage of electrical current to the metal without the coating being a barrier to such passage;

(b) impressing a series of direct current electrical potentials upon each of the respective coated areas in sequence and upon the respective associated working electrode to enable current to flow between the metal article in the electrochemical cell and the counter-electrode; and (c) measuring the current flow as the direct current potential is varied relative to the reference electrode to generate a potentiodynamic scan of the active and passive regions of the metal.

14 Claims, 6 Drawing Sheets

OTHER PUBLICATIONS

T. Bein, "Efficient Assays for Combinatorial Methods for the discovery catalysts", Angew. Chem. Int. Ed. 1999, month unavailable, vol. 38, No. 3, pp. 323–326.

"Combinatorial Chemistry: Materials Entrants Take on Symyx", Chemical Week, Aug. 11, 1999, pp. 27–29 and 32.

"Combinatorial Chemistry Comes of Age", Chemical Engineering, Sep. 1999, pp. 76–80.

A. Metrot, "A Simple Nondestructive Electrochemical Method to Test the Barrier Resistance of Organic Coatings", Journal of Applied Electrochemistry 26 (1996), month unavailable, pp. 361–363.

H.F. Clay "Polarisation Techniques for the Study of Corrosion Inhibition and their Application to Painted Specimens", J. Oil Color Chem. Assn. (1965), month unavailable, vol. 48, pp. 356–381.

H.F. Clay "A method for the Application of Polarisation Techniques to the Study of the Inhibition of Corrosion by Paint Films", Chemistry and Industry, Feb. 17, 1962. pp. 306–307.

J. Wolstenholme, "Electrochemical Methods of Assessing the Corrosion of Painted Metals—A Review", Corrosion Science, 1973, month unavailable, vol. 13, pp. 521–530.

* cited by examiner

HIGH THROUGHPUT ELECTROCHEMICAL TEST FOR MEASURING CORROSION RESISTANCE

RELATED APPLICATIONS

This application is a continuation-in-part of copending U.S. Ser. No. 08/852,649, filed May 7, 1997 and also claims the benefit of U.S. Provisional Ser. No. 60/106,525, filed Oct. 31, 1998.

BACKGROUND OF THE INVENTION

The use of various electrochemical techniques to quantify the corrosion of a metal article or to measure the effectiveness of a given corrosion inhibition technique has been described in a number of references including the following: H. P. Hack, "The Potentiostatic Technique for Corrosion Studies", p. 57 in Electrochemical Techniques for Corrosion Engineering, R. Baboian, ed., National Association of Corrosion Engineers, Houston 1986; J. R. Scully, Corros. Tests Standard 75–90. (R. Baboian, ed.) American Society for Testing and Materials: Philadelphia, Pa., 1995 (CAS Ref.: 125:259468); G. R. Cameron et al., Electrochemical Techniques for Corrosion Engineering, p. 183; J. Wolstenholme, Electrochemical Methods of Assessing the Corrosion of Painted Metals—A Review", Corrosion Science 13, 521 (1973), G. W. Walter, "A Critical Review of d.c. Electrochemical Tests for Painted Metals", Corrosion Science 26, 39 (1986), and J. N. Murray, "Electrochemical Test Methods for Evaluating Organic Coatings on Metals: an Update, Parts I, II, and III, Progress in Organic Coatings 30, 225 (1997), ibid. 31, 255 (1997), and ibid. 31, 375 (1997).

Such techniques divide broadly into those that interrogate the chemistry of metal and those that interrogate the quality of the organic coating. Despite the widespread use of organic or resinous coatings to protect corrosion-prone metals, such as steel and aluminum, from deterioration, it has not been standard practice to interrogate electrochemically or otherwise a metal substrate beneath an organic coating. Several recently reported methods are generally relevant to the method described herein without being suggestive thereof: electrochemical noise spectroscopy has been adapted to study underpaint corrosion (L. Meszaros et al., FATIPEC Congr., 22nd (Vol. 4), 68–71, 1994 (CAS Ref.: 124:12877)); measurement of the corrosion resistance of painted metal (M-H Khireddine, Mater. Tech. (Paris) 84, 3–8, 1996 (CAS Ref.: 125:174734)); the use of electrochemical impedance spectroscopy (EIS) for evaluation of underpaint corrosion is reported (P. L. Bonora et al., Electrochim. Acta 41, 1073, 1996; F. Mansfield, ACH—Models Chem., 132, 619, 1995 (CAS Ref.: 124:63152)); and EIS has also been adapted for measurement of the corrosion rates of uncoated steel alloys (A. Nishikata et al., Corros. Sci. 37, 2059, 1995 (CAS Ref.: 124:62557)). EIS is more commonly used to evaluate the integrity of paint coatings on metal substrates by analyzing the coating as an element in an electronic circuit. Reviews of the use of EIS for the evaluation of coatings can be found in the following publications: G. W. Walter, Corrosion Science 1986, 26, 681; and F. Geenan, National Technical Information Service (Order No. PB2-133479).

An electrochemical method for measurement of the barrier resistance of organic coatings (A. Metrot et al., J. Appl. Electrochem. 26, 361, 1996 (CAS Ref.: 124:273062) is also relevant to but distinct from the method described herein.

SUMMARY OF THE INVENTION

The present invention is a high throughput electrochemical test method for determining the resistance to corrosion of a metal article coated with a "library" of one or more differing coatings compositions containing candidate corrosion inhibitors. The process comprises:

(a) making, as the working electrode in an electrochemical cell which also comprises a reference electrode, a counter-electrode and an electrolytic solution, one or more metal articles comprising a plurality of coated areas thereon, with the proviso that a portion of the coating does not exist on the metal thereby allowing for the ultimate passage of electrical current to the metal without the coating being a barrier to such passage;

(b) impressing a series of direct current electrical potentials upon each of the partially coated metal articles in sequence to enable current to flow between the metal article under test in the electrochemical cell and the counter-electrode; and (c) measuring the current flow as the direct current potential is varied relative to the reference electrode to generate a potentiodynamic scan of the active and passive regions of the metal.

It is within contemplation of the present invention that, e.g., within a series of related samples, one need measure current density at only one or several anodic bias potentials, to determine the relative merit of candidate inhibitor compositions. That is, one may achieve the desired purpose without running a complete polarization curve.

A procedure such as this where the applied potential is held constant and current is allowed to respond is characterized as a "potentiostatic" procedure. If the voltage regulating potentiostat is programmed to hold a potential for some period of time, then change to and hold a new potential, the method is called "potentiodynamic". Methods in which applied voltages are increased in a positive or anodic sense are called "anodic" scans.

In the alternative, a polarization scan can be run in a galvanostatic mode: a series of currents can be imposed and the voltage measured. However, galvanostatic methods would be expected to be inferior for the intended purpose to potentiostatic methods.

In *Principles and Prevention of Corrosion*, Second Edition (1996, Prentice Hall, Upper Saddle River, N.J., page 123), Denny A. Jones reviewed experimental methods for measuring active-passive metals:

. . . controlled current instrumental methods are not adequate for determining active-passive behavior, and controlled potential methods are required to show the entire anodic polarization curve.

It is apparent that galvanostatic procedures are inadequate to define the active-passive curve properly because potential is not a single-valued function of current. However, current is a single-valued function of potential, and controlled potential procedures . . . are effective in studying the electrochemical behavior of active-passive alloys.

DESCRIPTION OF THE DRAWINGS

The present invention is further illustrated by the Drawings, which form a portion of the present specification, wherein.

DESCRIPTION OF THE PREFERRED EMBODIMENTS

Figure 1:
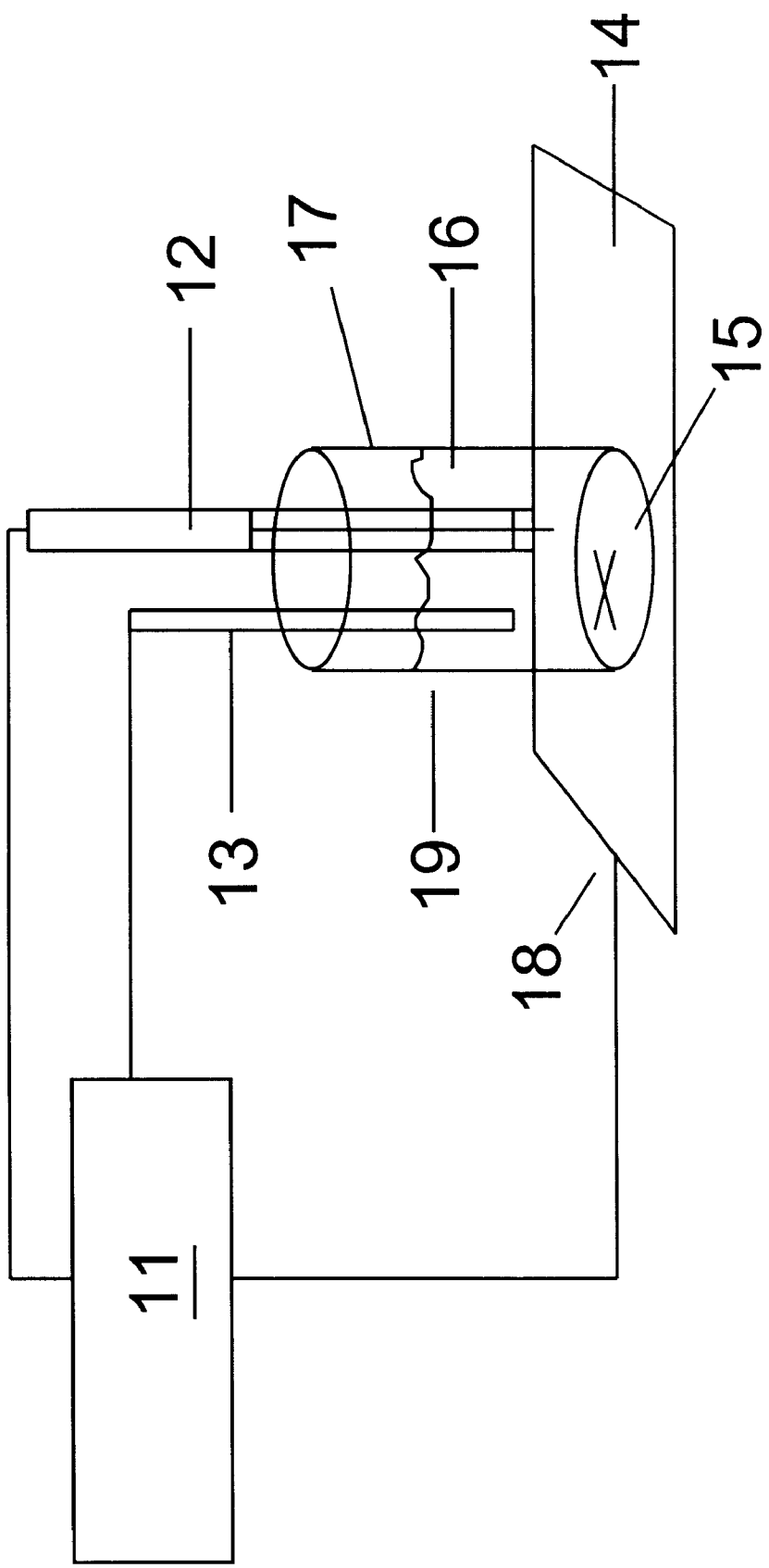
FIG. 1 is a schematic view of an apparatus for practice of the present invention.

This invention concerns, in one embodiment, a DC potentiodynamic method, which has been largely used in the development and characterization of uncoated metals and alloys (E. D. Verink, Jr., Electrochemical Techniques for Corrosion Engineering, p. 101), to the measurement of metals coated with an organic or resinous coating or other corrosion-inhibiting formulation in a novel manner. The aforementioned reference to A. Metrot et al. in the section dealing with the background of the present invention, although being used with coated metal test specimens, measured the barrier resistance of the coating in a nondestructive manner without measuring the capability of the coating to passivate areas from which the coating had been removed.

It is proposed that this method is useful in predicting and quantifying the effectiveness of organic coatings applied for the purpose of corrosion protection of metal including the circumstance in which a portion of the coating has been removed from the metal substrate or for measuring the protection provided by the coating to portions of the metal not directly covered by the coating. In the practice of this invention, substrate metal coated with a plurality of corrosion-preventing coating areas and, optionally, topcoat is made to be the working electrode of an electrochemical cell; a range of increasingly positive electric potentials relative to a reference is imposed on the working electrode (coated substrate), and currents between the working electrode and an inert counter-electrode, corresponding to the various potentials, are measured through the active and passive regions of the metal. The current-voltage curve generated in this manner is highly instructive of the corrosion preventing and particularly the metal-passivating capability of the coating.

An alternate arrangement is to provide a plurality of metal coupons each with its individual coated and uncoated domains, as previously described for the plurality of coatings/single metal coupon configuration.

The use of this technique relies on the possibility of electrical current between working and counter electrodes. To the extent that an organic or resinous coating is electrically insulating and without defect, a coated metal substrate cannot be evaluated with this method. In one embodiment, a score mark or positive pinhole defect through the coating and exposing bare metal may be made, for example, by means of a knife or drill prior to measurement of the current-voltage curve. Alternatively, the area of the coating (of any desired shape or position) can be deliberately fashioned or designed so that there will remain an adjacently situated uncoated metal area when the otherwise coated metal sample is later tested electrochemically in accordance with the present invention, as will be described in more detail hereinafter. It is only essential that there be an uncoated portion of the metal adjacent to the coating in the electrochemical cell for the testing procedure.

FIG. 1 provides a schematic view of one a particular apparatus that can be used to practice the current method with only one coated area being shown. Commercially available electrochemistry measuring apparatus of this type that have been used to test uncoated metal specimens are available, for example, from Gamry Instruments, Inc., Warminster, Pa. (the CMS 105 DC Corrosion Measurement System). As FIG. 1 herein depicts, a potentiostat 11, reference electrode 12, counter-electrode 13, and coated metal sample 14 are provided with a scratched portion 15 of the metal sample 14 residing in an electrolyte solution 16 contained in a suitable non-conductive container 17 which is preferably made of glass.

The electrochemical test method for determining the resistance to corrosion of the coated metal article 14 comprises, in one embodiment: making a portion of that coated metal article, from which a portion 15 of the coating has been removed to allow for the ultimate passage of electrical current therethrough, the working electrode 18 in an electrochemical cell 19 which also contains a reference electrode 12, a counter-electrode 13 and an electrolytic solution 16; impressing a series of direct current electrical potentials upon the working electrode 18 to enable current to flow between the metal article in the electrochemical cell 19 and the counter-electrode 13; and measuring the current flow as the direct current potential is varied relative to the reference electrode. In the present method, the working electrode is always the coated metal article under test, but the reference and counter-electrodes can be varied, if desired. Representative reference electrodes include the saturated calomel, normal hydrogen, and platinum electrodes, while the counter-electrode can, for example, be a graphite or platinum electrode.

Figure 2:
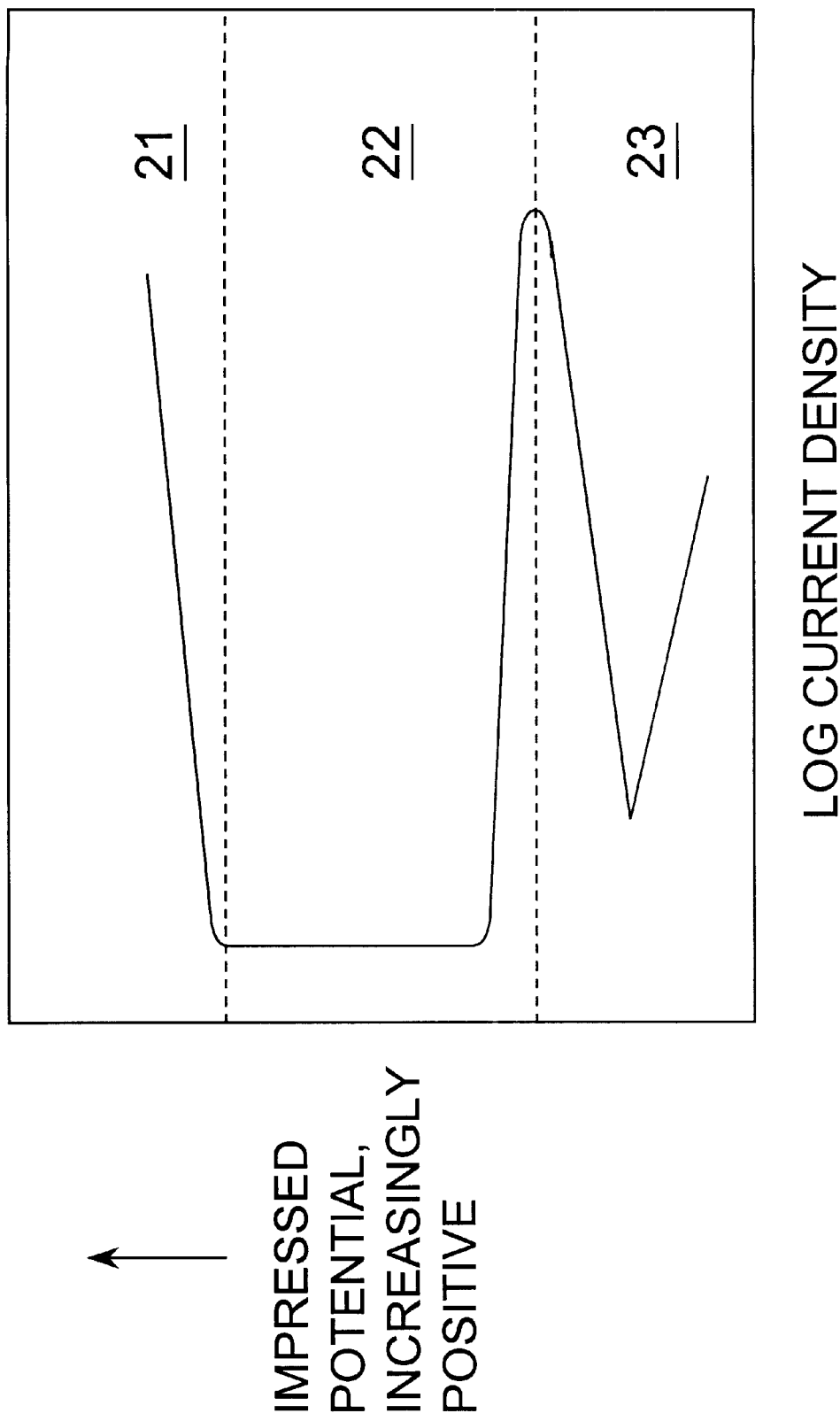
FIG. 2 is an ideal potentiodynamic scan for an active-passive metal.
Figure 3:
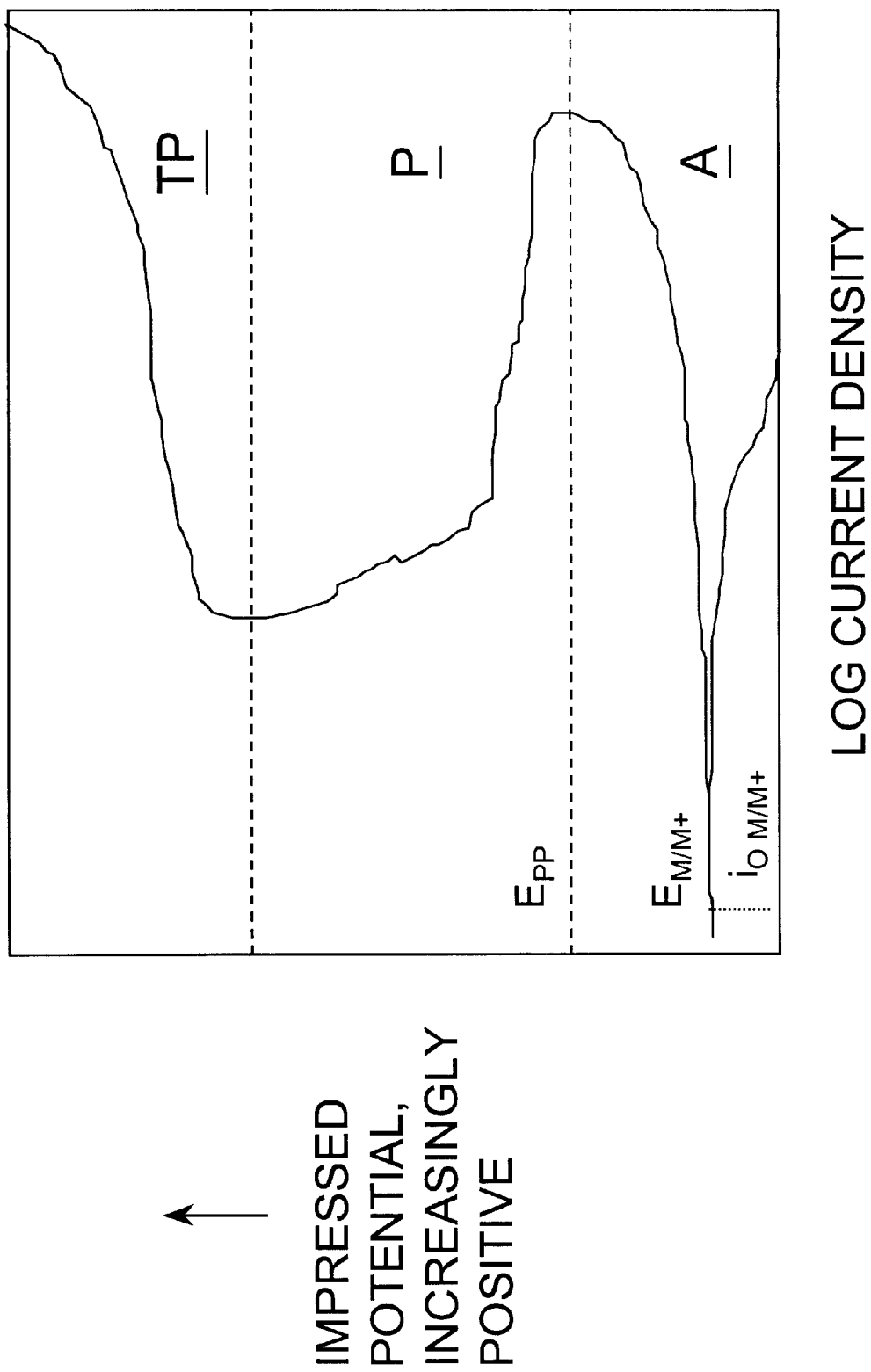
FIG. 3 is an actual potentiodynamic scan for coated metal in accordance with the present invention.

FIGS. 2 and 3 illustrate, respectively, the type of potentiodynamic scan for uncoated metal (as illustrated by M. G. Fontana et al., Corrosion Testing, 1986, FIGS. 9–25) and for coated metal in accordance with the present invention. In FIG. 2 the transpassive region of the scan is represented by reference numeral 21, with the passive and active regions of the scan being represented by 22 and 23, respectively.

Using the ideal plot of FIG. 2 as a model, the experimental scan depicted in FIG. 3 can be evaluated to determine a sample's potential resistance to corrosion. In FIG. 3, $E_{M/M+}$ represents the open circuit potential and $i_{oM/M+}$ represents the open circuit current characteristic of the sample. At potentials near $E_{M/M+}$ the metal follows typical Tafel behavior with the rate of dissolution of the metal increasing exponentially with potentials applied to the sample positive of the open circuit potential. This is the active region (labeled "A" in FIG. 3). At positive potentials (anodic) of the open circuit potential, there is oxidation of the metal. In the depicted apparatus, the rate of oxidation of the metal is proportional to the current density. An active-passive metal is characterized by $E_{PP}$, the primary passive voltage and a corresponding $I_c$, the critical anodic current density for passivity. The point where current density begins to decrease with increasing potential is the active-passive transition of the sample under test. The decrease in current density is thought to result from formation of an insulating oxide film on the metal surface. In the passive region (labeled "P" in FIG. 3), the current (rate of corrosion of the metal) decreases to some value which is relatively constant and is characteristic of the passivity of the sample under test. The transpassive region (labeled "TP" in FIG. 3), where the rate of dissolution of metal again increases with increasing potential at high anodic potentials, is thought to result from destruction of the metal's protective oxide layer.

The present process can be used to screen for potentially valuable corrosion protection additives by incorporating such additives in a series of coated metal samples that are configured as described herein and then tested. While one could screen such samples one at a time in series using a single electrochemical cell, present day high throughput technologies (also referred to as "combinatorial methods") which make possible more rapid screening of samples. In such methods, an automated or robotic system individually addresses each of a large number of pigment or paint formulations which have been prepared as a collection or "library" of individual samples (preferably also prepared with combinatorial technologies) on a substrate metal. The robot-like mechanism sequentially tests, one at a time, a small area of uncoated metal and an adjacently situated larger area of metal covered by a particular pigment or formulation containing a candidate corrosion inhibitor additive or additives in an electrochemical cell. The test machine would be programmed to run a DC potentiodynamic scan, as earlier described, at each such position so that each such scan affords a measure of the degree of passivation of the metal conferred by each candidate corrosion inhibitor. The advantage of this high throughput embodiment of the present invention is to allow for the rapid screening of many corrosion inhibitor candidates within a very much shorter time frame than allowed for by existing technologies. For example, libraries of metal oxide compounds, even if prepared for other purposes, could be screened for effectiveness in anticorrosion coating formulations.

The type of robot-like machine that can be adapted for use with the particular electrochemical cell and test configuration of the present invention is known in the art for other types of high throughput sample preparation and testing. Examples of such robotic apparatus that can be modified to hold the particular electrochemical cell and related test apparatus are available: Bohdan Neptune (Bohdan Automation, Inc., Vernon Hills, Ill.); Argonaut Surveyor (Argonaut Technologies, San Carlos, Calif.); and the like.

R. B. van Dover et al. described use of a scanning Hg-probe that was used for screening the electrochemical properties of libraries of new dielectric compositions. (Combinatorial Chemistry 61, 217 (1999), esp. p. 220)

A mercury-filled capillary was positioned in light contact over a sample to be tested. At each position, the Hg-probe, the material under test, and the conductive substrate beneath the material formed a metal-oxide-metal (M-O-M) capacitor whose dielectric properties were measured. A current-voltage curve was measured at each position, before the Hg-electrode was translated to a new position, the location of a different member of a dielectric materials library, and a new scan measured and recorded.

We propose to test electrochemically libraries of metal-protecting coating compositions in a similar manner: just as an Hg-probe was translated from one dielectric composition to another, in the present invention, an electrolytic cell will move from a site of one coatings composition to the site of another, testing and recording electrochemical data of each. At each composition, an electrochemical cell will form with electrolyte and counter and reference electrodes. As in the cited example, a current-voltage curve will be measured and stored at each composition.

Figure 4:
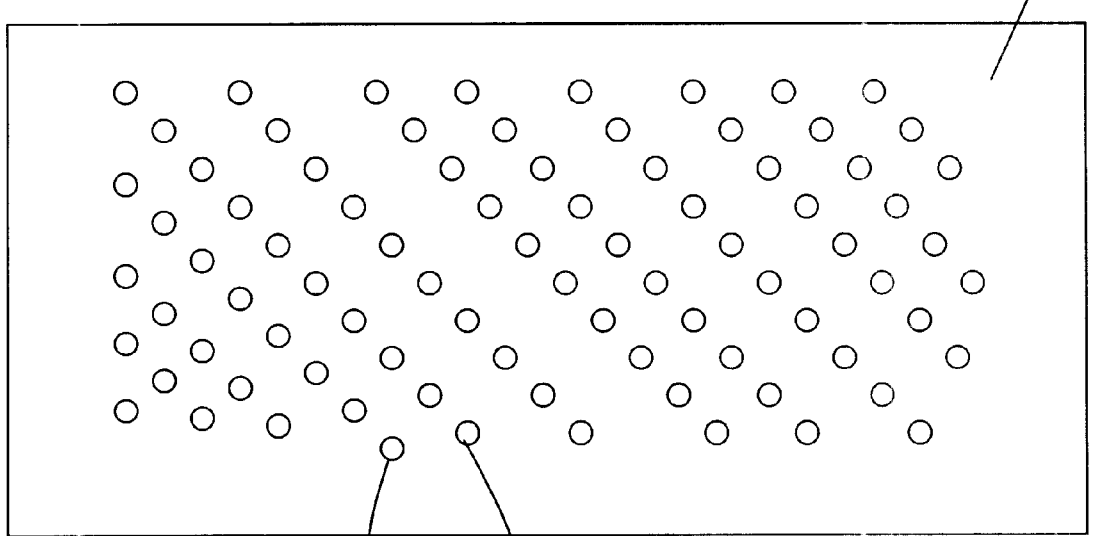
FIG. 4 is an overhead view of a metal article containing a plurality of differing pigment or paint formulations for use in a high throughput screening operation.
Figure 5:
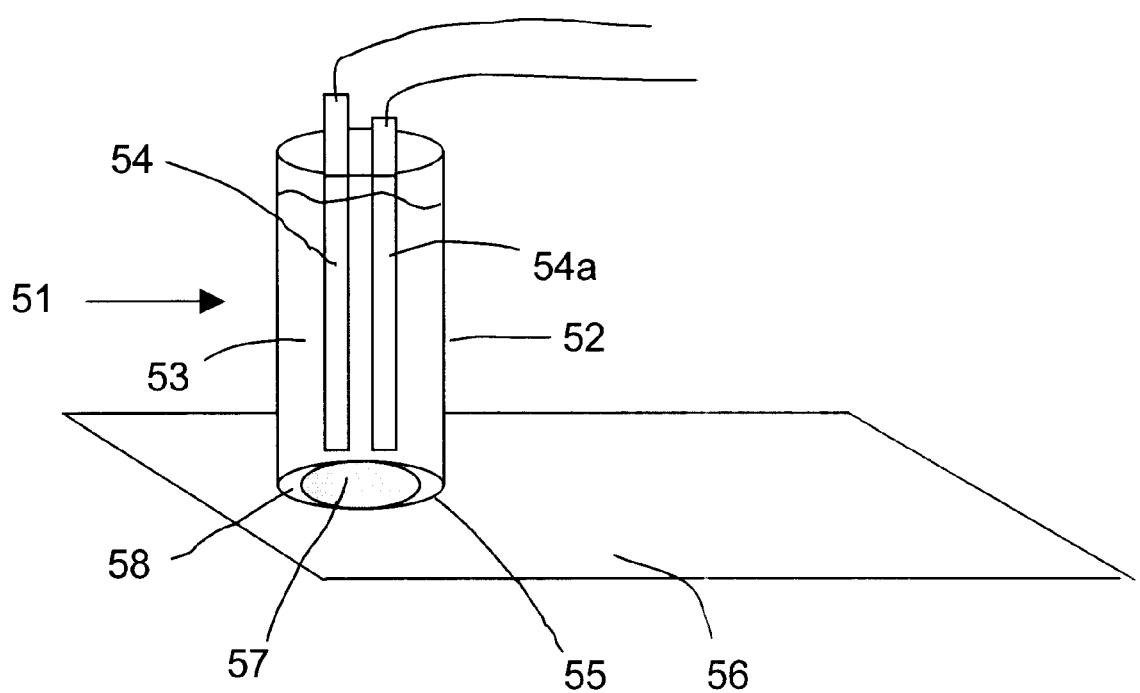
FIG. 5 shows an individual electrochemical cell suitable for use with type of article shown in FIG. 4 in a high throughput screening operation.
Figure 6:
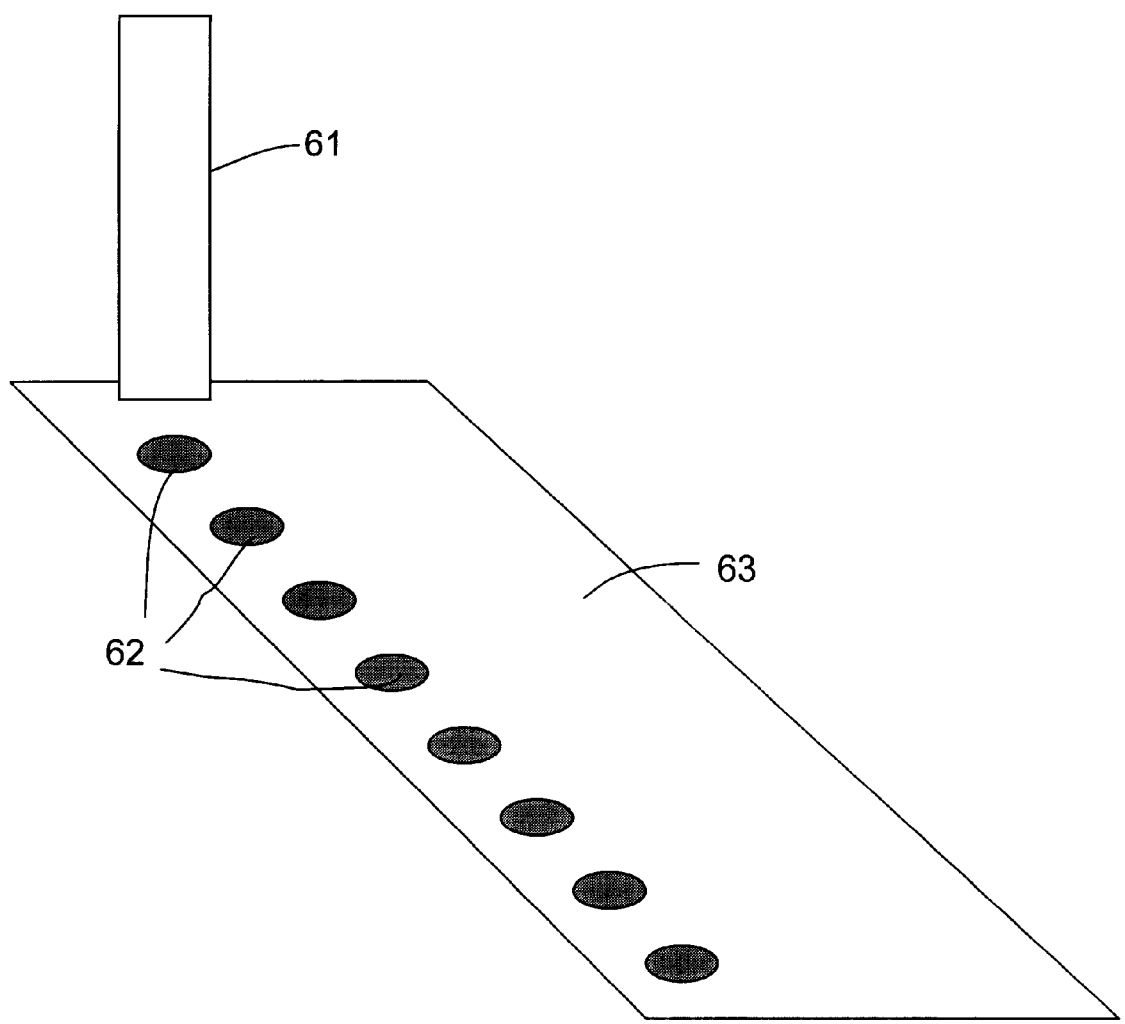
FIG. 6 illustrates the glass cylinder in the cell depicted in FIG. 5 approaching a series of individual pigment or paint formulations as more fully shown in FIG. 4 in a high throughput screening operation.

More particular examples of apparatus that can be used in the technique of the present invention are illustrated in FIGS. 4–6 wherein a single metal coupon 41 can carry a plurality of coating areas 42, each containing differing corrosion inhibitor candidates and each having an opening to the metal surface as an electrochemical cell, for example, interrogates a series of the respective cells in a high through-put operation. Such a design allows for the efficient screening of large numbers of candidate corrosion inhibitor candidates in an economical manner. FIG. 5 depicts the type of individual cell 51 that can be used. It comprises a cylindrical body 52 containing electrolyte solution 53, reference and counter electrodes 54 and 54a and an o-ring seal 55 between the cylindrical cell 52 and the metal coupon 56 carrying the pigment or coating candidate 57 to be tested. There is an uncoated area 58 outside the candidate formulation 57 to allow a path for the electric current to the bare metal. FIG. 6 illustrates, in schematic fashion, the glass cylinder 61 approaching a series of pigment or coating formulations 62 on the metal coupon 63.

The foregoing illustrates the current invention in its potentiodynamic mode. As earlier indicated, it can be used in its galvanostatic mode where a series of differing currents is applied and the voltage change is monitored.

The present invention is further illustrated by the Examples that follow.

EXAMPLE 1

This Example illustrates the coating of aluminum coupons with poly (2,6-dimethylphenylene oxide) and comparing the DC potentiodynamic behaviors of coated and uncoated coupons.

Unpretreated aluminum coupons (designated "ACT aluminum 6061T6 03×06×032 cut only; unpolish") were obtained from ACT Laboratories, Inc., Hillsdale, Mich. 49242-0735 and were cleaned with acetone and methylethylketone (MEK) scrubbing. A coating solution was formed by blending 10 g of BLENDEX BHPP 820 brand of poly (2,6-dimethylphenylene oxide) (PPO), obtained from General Electric Specialty Chemicals, Parkersburg, W.Va., with gentle heating, in 90 g of toluene. The resulting PPO-toluene solution was then filtered through a 0.45 micron PTFE filter, was barcoated onto aluminum coupons with a #24 wire wound rod, and was baked for five minutes at 200° C. in a forced air oven. After baking, the coupons were immersed in room temperature water and were then dried in air. Aluminum coupons which had been cleaned with solvent but not otherwise treated were also measured by the technique of the present invention.

In the DC potentiodynamic technique described earlier, the coated aluminum coupon was made the working electrode of an electrochemical cell. A graphite rod was the counter electrode; a saturated calomel electrode (SCE) was the reference. Increasingly positive potentials were imposed on the working electrode, and current density between working and counter electrodes was measured. Low current density in the region of 0 to +1 V vs. SCE was judged as evidence of a diminished tendency to corrosion. Any abrupt increase in current density at relatively positive applied voltages was correlated to pitting of the metal surface; pits formed in this way could be seen without magnification. The high current density at relatively low applied voltage was further correlated to extensive pitting.

Current-voltage plots were generated for samples: (A), an aluminum coupon with no polymer coating; and (B), aluminum with a poly(2,6-dimethylphenylene oxide) coating, film thickness under 0.1 mil. The data indicated in two ways that poly(2,6-dimethylphenylene oxide) afforded pitting protection to the substrate metal: the current density in the entire applied voltage region (−1.5 to +1 V vs. SCE) was about two orders of magnitude lower, and (ii) in the region −0.5 to +1.0 there was no abrupt increase in current density in the coated sample as there was evident in the spectrum of the uncoated sample. Inspection of the coupons after testing confirmed the spectra: pits were clearly evident in the uncoated coupon but were not evident in the coated coupon.

EXAMPLE 2

In this Example, cold rolled steel (CRS) was coated with a clear or pigmented epoxy-melamine coating and measurement of the DC current-voltage behavior was measured.

ACT cut only unpolished cold rolled steel coupons were cleaned of shop oil and grit with acetone and MEK scrubbing. Epoxy-melamine primer paints suitable for coating on a steel substrate were prepared in the following manner: bases of various "pigments", including Monsanto VERSICON brand polyaniline emeraldine base ("PANI-EB") and General Electric BLENDEX BHPP 820 brand poly (2,6-dimethylphenol) ("PPO") were ground; were then dispersed, using a high speed sand grind mixer, in a 40% solids solution of an advanced, 9-type epoxy resin (Akzo Nobel HV 6156 brand). Then, MEK and A-100 solvents were added, as needed, to ensure formation of homogeneous dispersions. Typically, 41.6 g of "pigment" was added to 208 g of epoxy resin solution, to which 97.7 g of A-100 and 14.3 g of MEK solvents were added. Aliquots of the various grind bases were taken and diluted with epoxy resin solution and with CYMEL 380 brand melamine solution to form pigment:binder concentrations ("p/b") of 0.44, 0.22, and 0.15 on a weight basis. In addition, samples were prepared from unpigmented or "clear" epoxy-melamine solution and from strontium chromated pigmented epoxy-melamine (Akzo Nobel 9X444 brand).

The paint formulations described above were applied to the cleaned steel substrate with a #14 wire wound rod, the resulting samples were then baked to a 420° F. peak metal temperature, and they were then quenched by immersion in tap water.

Using the DC potentiodynamic technique of this invention, each coated steel coupon was again made the working electrode of an electrochemical cell, with a graphite rod counter electrode, and a saturated calomel electrode reference. Each coating was scored in the region of measurement with a knife-edge, forming an "X" (1.5 cm for each score)to expose the bare metal. In this testing, 0.1 N $NaHCO_3$ was the electrolyte. In the course of measurement, increasingly positive potentials were imposed on the working electrode, and the current density between the working and counter electrodes was measured. Low current density in the region of 0 to +1 V vs. SCE was taken as evidence of diminished tendency of the sample to corrode.

Current-voltage plots were generated for samples:(C), steel with clear epoxy-melamine primer; (D), steel coated with chromated epoxy-melamine primer; (E), steel coated with epoxy melamine and PPO pigment; (F), steel coated with epoxy melamine and PANI-EB pigment; and (G), steel coated with epoxy melamine and VERSICON pigment.

The data indicated in two ways that various pigments afford corrosion protection to the substrate steel: the open circuit potential of the unpigmented coated sample (C) was relatively negative (−0.70 V), and the current density in the region 0 to +1 V vs. SCE was high (about $10^{-3}$ $A/cm^2$); the chromate-coated sample had a relatively positive open circuit potential (−0.45 V) and low current density (about $10^{-6}$ $A/cm^2$); samples coated with either PPO (E) or PANI-EB (F) pigmented epoxy-melamine showed an active-passive transition at an applied voltage of about −0.4 V and a passive region of low current density (about $10^{-5}$ $A/cm^2$) in the region 0 to +1 V of applied voltage. The sample coated with the VERSICON brand pigment (G) did show an active-passive transition at about −0.3 V but had a rather high current density (about $10^{-3}$ $A/cm^2$) in the passive region.

The forgoing Examples, since they merely illustrate certain embodiments of the present invention, should not be used to construe the present invention in a limiting fashion. The scope of protection sought is set forth in the Claims which follow.

I claim:

1. A high throughput electrochemical test method for determining the resistance to corrosion of a metal article coated with a plurality of corrosion preventing coated areas which comprises:

(a) making, as the working electrode in an electrochemical cell, which also comprises a reference electrode, a counter-electrode and an electrolytic solution, one or more metal articles each comprising the plurality of coated areas thereon, with the proviso that there is an uncoated area of metal adjacent a coated area thereby allowing for the ultimate passage of electrical current to the metal without the coated area being a barrier to such passage;

(b) impressing a series of direct current electrical potentials or a series of direct current flows, respectively, upon each of the respective coated areas in sequence and upon the respective associated working electrode to enable current to flow between the metal article in the electrochemical cell and the counter-electrode; and (c) measuring the current flow as the direct current potential is varied relative to the reference electrode or measuring the voltage as the direct current flow is varied relative to the reference electrode, respectively, to generate a potentiodynamic scan or potentiostatic scan, respectively, of the active and passive regions of the metal.

2. A method as claimed in claim 1 wherein the coated area comprises at least one corrosion inhibiting additive.

3. A method as claimed in claim 1 wherein the metal is steel.

4. A method as claimed in claim 1 wherein the coated area comprises at least one corrosion inhibiting additive and the metal is steel.

5. A method as claimed in claim 1 wherein the reference electrode is a saturated calomel electrode.

6. A method as claimed in claim 1 wherein the counter-electrode comprises graphite and the reference electrode is a saturated calomel electrode.

7. A method as claimed in claim 1 wherein the reference electrode is a saturated calomel electrode, the working electrode comprises coated steel, and the counter-electrode comprises graphite.

8. A method as claimed in claim 1 wherein the coated area comprises at least one corrosion inhibiting additive, the reference electrode is a saturated calomel electrode, the working electrode comprises coated steel, and the counter-electrode comprises graphite.

9. A method as claimed in claim 1 wherein the metal is steel, the reference electrode is a saturated calomel electrode, the working electrode comprises coated steel, and the counter-electrode comprises graphite.

10. A method as claimed in claim 1 wherein the coated area comprises at least one corrosion inhibiting additive, the metal is steel, the reference electrode is a saturated calomel electrode, the working electrode comprises coated steel, and the counter-electrode comprises graphite.

11. A method as claimed in claim 1 wherein the metal is aluminum.

12. A method as claimed in claim 1 wherein the metal is aluminum, the working electrode comprises coated aluminum and the counter-electrode is selected from the group consisting of graphite and platinum.

13. A method as claimed in claim 1 wherein the coated area comprises at least one corrosion inhibiting additive, the metal is aluminum, the working electrode comprises coated aluminum and the counter-electrode is selected from the group consisting of graphite and platinum.

14. A high throughput electrochemical test method for determining the resistance to corrosion of a metal article coated with a plurality of corrosion preventing coated areas which comprises:

(a) making, as the working electrode in an electrochemical cell, which also comprises a reference electrode, a counter-electrode and an electrolytic solution, a single metal article that contains a plurality of coated areas thereon, with the proviso that there is an uncoated area of metal adjacent a coated area thereby allowing for the ultimate passage of electrical current to the metal without the coated area being a barrier to such passage;

(b) impressing a series of direct current electrical potentials or a series of direct current flows, respectively, upon each of the respective coated areas in sequence and upon the working electrode to enable current to flow between the metal article in the electrochemical cell and the counter-electrode; and (c) measuring the current flow as the direct current potential is varied relative to the reference electrode or measuring the voltage as the direct current flow is varied relative to the reference electrode, respectively, to generate a potentiodynamic scan or potentiostatic scan, respectively, of the active and passive regions of the metal.

* * * * *